United States Patent [19]
Knutson

[11] Patent Number: 5,975,906
[45] Date of Patent: Nov. 2, 1999

[54] SOFT POLYMER DENTAL STRIP AND PROCESS THEREFOR

[76] Inventor: Eric J. Knutson, 11443 Hesperian Cir., Gold River, Calif. 95670

[21] Appl. No.: 08/931,662

[22] Filed: Sep. 16, 1997

[51] Int. Cl.$^6$ ..................................................... A61C 5/10
[52] U.S. Cl. ..................... 433/226; 433/39; 128/DIG. 14
[58] Field of Search .................................. 433/34, 37, 39, 433/40, 48, 226; 128/DIG. 14

[56] References Cited

U.S. PATENT DOCUMENTS

| | | | |
|---|---|---|---|
| 3,108,377 | 10/1963 | Meyer | 433/39 |
| 3,218,374 | 11/1965 | Perbohner et al. | 264/17 |
| 3,421,222 | 1/1969 | Newmann | 433/226 |
| 4,563,152 | 1/1986 | McClure | 433/39 |
| 4,685,969 | 8/1987 | Schmid et al. | 106/35 |
| 4,704,087 | 11/1987 | Dragan | 433/39 |
| 4,718,849 | 1/1988 | von Weissenfluh et al. | 433/39 |
| 5,035,615 | 7/1991 | Din | 433/39 |
| 5,385,469 | 1/1995 | Weissman | 433/40 |
| 5,403,885 | 4/1995 | Voigt et al. | 542/731 |
| 5,788,487 | 8/1998 | Meyer | 433/39 |

OTHER PUBLICATIONS

Pitel, Mark L., "Indirect–Composite Inlays/Onlays II: A Comparison of Generally Recognized Clinical Techniques," Esthetic Dentistry Update, vol. 5, No. 6, Dec. 1994, pp. 138–143.

Stean, Howard, "PTFE Tape: A Versatile Material in Restorative Dentistry," Dental Update, vol. 20, No. 4, May 1993, pp. 146–148.

*Primary Examiner*—Ralph A. Lewis

[57] ABSTRACT

A dental strip comprised of uniformly thick, dead soft polymer, for use as a matrix in molding hardenable restorative materials. Matrixing processes for the strip permit the formation of interproximally contacting restorations without wedging; and the formation of composite restorations with smooth interproximal margins. Other processes for the strip permit the formation of removable restorations which are separated from prepared tooth surfaces by the strip; the formation of restorations with reduced resin excess; and stabilization of the strip on dental surfaces by affixing with a temporary adhesive.

18 Claims, 3 Drawing Sheets

SOFT POLYMER DENTAL STRIP AND PROCESS THEREFOR

BACKGROUND

1. Field of Invention

This invention relates to dental restorations, specifically to the contouring of restorative material utilizing matrices and burnishable.

2. Description of Prior Art

Dental matrices of the art are flat, flexible strips of material which may be contoured into shapes which resemble surfaces of teeth. Matrix strips are manipulated to approximate the desired shape of the restoration. The strips provide a contourable surface, whereby hardenable restorative materials may be partially contained and manipulated into desirable contours prior to hardening. Matrices of the art are comprised of flat strips of thin steel, flat strips of mylar, or other similar materials.

The metal strips have a thickness ranging from 0.001 to 0.002 inches. Metal matrices are used more often for restoring posterior teeth, as they are less likely to tear than transparent strips.

Transparent strips are primarily used as matrix strips for esthetic restorations. Theses are typically comprised of 0.002 inch thick acetate, known as Mylar (3M). The transparency provides access for the curing light, as the strip frequently covers the restoration.

Metal and Mylar strips of less thickness than those cited tend to wrinkle or tear, such as when fitting through interproximal contact areas between teeth. It is not practical for a dentist to reduce the thickness of mylar or metal strips, such as by burnishing.

Metal and transparent strips are typically flat, and relatively stiff, and exhibit substantial memory for their shapes. As a result, they readily cut the interproximal gingival papilla, and initiate bleeding. Bleeding is a major impediment for restoration bond strengths and esthetics. Matrix memory also tends to interfere with the operator's efforts to mold the restorative material to physiological contours. As such, restorations formed with matrices of the art tend to be molded somewhat nonphysiologically. This creates any of several problems, including overhangs, food traps, plaque and stain traps, open contacts, ledges, shredding dental floss, open embrasures, poor esthetics, chronic gingival inflammation, voids, and so on.

Further, matrices of the art must be forcefully retained against the critical gingival margin of a tooth cavity preparation as uniformly as is possible. Otherwise the matrix tends to pull away from the restorative material, and the margins. This requires a matrix retainer device, or a continuous operator finger pressure. Such retaining of matrices of the art interferes with the ease of molding restorative materials.

A wedge is used to conform matrix strips of the art, as much as possible, to the shape of the gingival margins of the preparation. However, portions of the strip tend to remain a distance from the preparation margins. This permits the restorative material to form undesirable overhangs along the preparation margins.

Wedges are used simultaneously to temporarily, slightly separate the teeth, to compensate for the thickness of the strip. Steel and Mylar matrices do not readily burnish to a reduced thickness. After the restoration is hardened, the strip is removed, and the teeth move back together. As such, the adjacent tooth is able to maintain proper contact with the restorative material. However, wedges tend to traumatize the interdental papillae, and promote bleeding.

Composites are hardenable restorative materials which contain adhesive resins. The curing, or hardening, of such resins is substantially inhibited in the presence of oxygen. An uncured oxygen inhibited resin layer, which forms at the exposed outer surface, facilitates strong bonding to subsequent additions of restorative material. Matrix strips of the art are nonporous, and thus shield the composite from oxygen. As such, they eliminate the oxygen inhibited layer. Further additions of unhardened restorative material to hardened, noninhibited surface material results in substantially weakened bond strengths.

In addition to contouring restorative materials, matrixes of the art also act as separators. Separators can be defined as any material or device which provides a barrier surface to prevent contact between substances. Separators include paints, gels, and strips of various materials. Howard Stean, in "PTFE Tape: A Versatile Material in Restorative Dentistry", DENTAL UPDATE, Vol. 20, No. 4, May 1993, discloses utilizing a soft polymer strip, PTFE (DuPONT Teflon® polytetrafluoroethylene), tape as a separator. Dr. Stean specifies utilizing the PTFE tape as a barrier to prevent inadvertent adhesion of luting cement with adjacent teeth, when cementing porcelain veneers. The PTFE tape is preferred as a separator because it can be burnished thin, to prevent displacement of porcelain veneers during cementation. In contrast, the thickness of the metal and mylar strips, as separators, would displace veneers from proper positioning on the teeth. As a result, the cleanup of hardened cement was made easier, without compromising the positioning of the veneers.

However, such use of PTFE tape for cementation of porcelain veneers never achieved widespread use for a variety of reasons. The thread seal tape commonly available in plumbing stores is fragile and difficult to use. Further, the process does not specify a technique for inserting the tape between interproximally contacting tooth preparations. Still further, current cementation technique prefers partly hardening the cement without any separator, followed by cleaning the excess cement, and completely hardening the remaining luting cement.

The above matrix strips suffer from a number of disadvantages:

(a) Matrix strip processes specify concurrent use of a wedge to mold a restoration to contact the adjacent tooth.

(b) Matrix strips are not readily burnishable to insubstantial thickness.

(c) The substantial shape memory of matrix strips tends to interfere with shaping unhardened restorative material.

(d) Matrix strips require applied tension to retain their position.

(e) Matrix strips tend to form overhanging restoration margins.

(f) Matrix strips substantially eliminate the oxygen inhibited layer of composite restorative materials.

(g) Matrix strips tend to cut the gingiva when placed to cover gingival margins.

(h) Matrix strips do not absorb bonding resins.

(i) No matrix strip process substantially blocks out all surface undercuts available to restorative material molded in a prepared tooth, and molded against substantially unshimmed interproximal contact areas.

(j) No matrix strip process provides a separating layer between surfaces of a prepared tooth and permanent restorative material against substantially unshimmed interproximal contact areas.

(k) No matrix strip process provides for molding restorative material in a prepared tooth, against substantially unshimmed interproximal contact areas, without unseating during a pliability stage, then hardened, and removed from the tooth, without substantial deformation, fracture, or abrading of the restorative material.

(l) No matrix strip process provides for molding restorative material by impression imprint in a prepared tooth, against substantially unshimmed interproximal contact areas, then hardened, and removed from the tooth, without substantial deformation, fracture, or abrasion.

(m) Processes utilizing matrix strips to form removable permanent restorations specify the use of separators which create separation spaces which are inconsistently too wide or too narrow.

A device similar to my matrix strip is not obvious because it is not readily apparent that a soft matrix strip can enhance contouring of restorative materials, especially without wedging, facilitate the formation of flush restoration margins, or be readily inserted into tightly contacting interproximal spaces. Neither is it apparent that a matrix strip can preserve the oxygen-inhibited layer of composite restorative materials, or that a semi-opaque matrix permits sufficient curing of light catalyzed restorative materials. Neither is it apparent that a soft polymer strip can permit accurate formation and removal of hardenable restorative material from a prepared tooth, or that stabilizing a soft polymer strip to dental surfaces is a valuable adjunct to dental processes.

OBJECTS AND ADVANTAGES

Accordingly, several objects and advantages of my invention are:

(a) to provide a matrix strip which permits the restorative material to contact the adjacent tooth without requiring the use of a wedge;

(b) to provide a matrix strip which is readily burnishable to insubstantial thickness;

(c) to provide a matrix strip which is dead soft, so that it adapts readily to the desired shape of the restoration, yet stabilizes the shape of the moldable restorative material;

(d) to provide a matrix strip which does not require applied tension to be retained in position;

(e) to provide a matrix strip which facilitates molding restoration margins without overhangs;

(f) to provide a matrix strip which substantially preserves the oxygen inhibited layer of composite restorative materials;

(g) to provide a matrix strip which does not tend to cut the gingiva when placed to cover gingival margins;

(h) to provide a matrix strip which absorbs bonding resins;

(i) to provide a matrix strip which is readily burnishable to insignificant thickness over the interproximal contact area, and separates restorative material from prepared tooth surfaces, such that the restoration is removable from the prepared tooth;

(j) to provide a matrix strip process that substantially blocks out all surface undercuts available to restorative material molded in a prepared tooth, and molded against substantially unshimmed interproximal contact areas;

(k) to provide a matrix strip process that specifies a separating layer between surfaces of a prepared tooth and permanent restorative material molded against substantially unshimmed interproximal contact areas;

(l) to provide a matrix strip process that specifies molding of restorative material in a prepared tooth, and against substantially unshimmed interproximal contact areas, without removal during a pliability stage, partial hardening of the restorative material, and removal of the hardened restorative material from the teeth without substantial deformation, fracture, or abrasion of such material;

(m) to provide a matrix strip process that permits impression imprint molding of unhardened restorative material in a prepared tooth, against substantially unshimmed interproximal contact areas, partial hardening of the restorative material, and then removal of the hardened restorative material without substantial deformation, fracture, or abrading of such material;

(n) to provide a process utilizing matrix strips to form removable permanent restorations that specifies the use of separators which create separation spaces which are consistently adequate;

(o) to provide a matrix strip process that specifies an interproximal contouring matrix for restorative materials, but leaves interproximal contact areas substantially unshimmed, such that a wedge is not needed;

(p) to provide a matrix strip which has an affinity for dental resins, and resin restorative materials.

Further objects and advantages are to provide a matrix strip which can transmit curing light, for hardening the restorative material. Still further objects and advantages will become apparent from a consideration of the ensuing description and drawings.

DRAWING FIGURES

Figure 1:
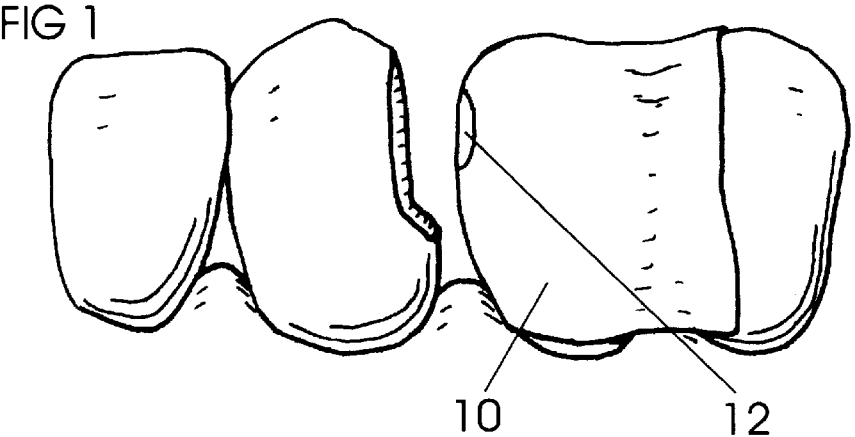
FIG. 1 shows a perspective view of a prepared tooth, which has lost interproximal contact with an adjacent opposing tooth, which is covered by a soft polymer matrix.

| Reference Numerals in Drawings | | | |
|---|---|---|---|
| 10 | strip | 12 | burnish |
| 14 | metal matrix | 16 | sectional matrix |
| 18 | retainer | 20 | roll |
| 22 | blockout | 26 | adhesive |

DESCRIPTION—FIGS. 1 TO 8

According to one aspect, the invention provides a process for molding a dental restoration on prepared tooth surfaces, wherein the restoration has interproximal contact with an adjacent tooth, comprising the steps of preparing the tooth surfaces, introducing the soft polymer strip matrix into the interproximal areas, introducing dental restorative material onto the prepared tooth surfaces, covering a portion of the restorative material with the soft polymer strip, molding the restorative especially by manipulation of the soft polymer strip as a dental matrixing means, hardening the restorative material, removing the soft polymer strip, and final shaping and finishing of the restoration.

According to another aspect of the invention, there is provided a soft polymer strip means for use in the process of the invention, shown in FIG. 1. FIG. 1 shows a perspective view of a prepared tooth, which has lost interproximal contact with an adjacent opposing tooth, which is covered by a soft polymeric strip. The soft polymeric strip, strip 10, is comprised of a dead soft polymeric material suitable for use a dental matrix, separator, or as a strip which is burnishable by applying pressure, said material having insignificant shape memory. It is burnishable to an insignificant thickness. Strip 10 also stretches readily, but resists tearing. It is preferred that strip 10 have microporosity, which permits the passage of gases, such as oxygen, and the absorption of resins. It is further preferred that strip 10 have an affinity for resin restorative materials, attracting them to its surface. Despite the porosity, strip 10 remains readily removable from hardened restorative materials, but leaves a surface with countless resin-tags, or protrusions, which further enhances the bond-strength of added restorative materials. It is still further preferred that strip 10 is semi-opaque, in contrast to matrices of the art, but has sufficient translucency to permit partial transmission of dental curing light. However, a range of transparency to semi-opacity is effective.

The preferred soft polymer strip 10 is porous, expanded polytetrafluoroethylene (PTFE) (DUPONT) sheeting, strip, or tape, made from a precursor unsintered PTFE. The preferred specifications for the tape are 10 mm wide, approximately 30 mm long, ranging in thickness from 80 to 85 microns, expanded within a range of 85% to 115%, wherein a typical pore measures 3 microns wide by 20 microns long, with pores having a wide range of sizes, having a density of 0.9 g/cc, and having a blue tint for visible light curing compatibility and for identification. However, other strip 10 specifications for width, length, thickness, density, expansion, pore size, color, and polymeric composition, such as other fluoroethylene polymers, can be effective. In contrast to the Gore tetrafluoroethylene polymers (W. L. Gore), expansion rates, temperatures, directions, and percentages preferred for the present invention enjoy a wider range of tolerances. In addition, post expansion annealing to increase crystallinity does not preserve preferred for strip 10 properties. For instance, 25 mm wide strip 10 is preferred for example 7 of the process. It is notable that, to the knowledge of Applicant, PTFE is not currently or routinely manufactured to preferred strip 10 specifications by any manufacturer for any other use. It is the opinion of Applicant that PTFE tapes available in plumbing stores are substantially inferior for performance of the dental processes described in this application, as well as for other dental procedures. As such, Applicant believes that strip 10 soft polymer material is marketable. Also, special preparation is indicated for oral use, such as gas sterilization, which would further differentiate it from commonly available PTFE tapes.

Strip 10 is shown covering the adjacent opposing tooth. There is no substantial contact between the prepared tooth and the adjacent opposing tooth. The length of strip 10 is oriented facial to lingual with respect to the dental arch, as it covers the interproximal portion of the adjacent opposing tooth. The facial and lingual trailing ends of strip 10 are shown pulled back and clinging to the facial and lingual surfaces of the adjacent opposing tooth, and the teeth beyond, prior to the final loading of hardenable restorative material into the prepared tooth.

Strip 10 has been burnished to an insignificant thickness, shown as burnish 12. Burnish 12 is over the interproximal contact area of the adjacent opposing tooth. The tooth is ready for the final loading of hardenable restorative material, such as thixotrophic composite.

Figure 2:
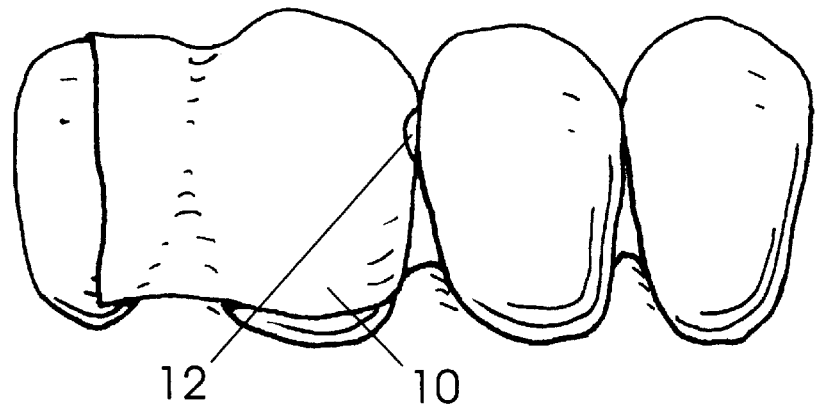
FIG. 2 shows a perspective view of a soft polymer matrix covering hardenable restorative material in a prepared tooth.

FIG. 2 shows a perspective view of a strip 10 covering the final load of hardenable restorative material in the prepared tooth. Strip 10 clings to the hardenable restorative material, and supports the molded shape, without applied tension that is typically required for matrices of the art. A matrix retainer or finger tension is notably absent. A wedge is also notably absent. The restorative material is against the interproximal contact area of the adjacent opposing tooth. Only the insignificant thickness of the burnish 12 area of strip 10 is interposed. The restorative material margins, particularly the gingival margins, are flush with the tooth preparation margins. No substantial overhanging restorative material margins remain, in contrast to matrices of the art. The restorative material is ready for hardening, such as by directing a curing lamp through strip 10. Oxygen is available to the surface of the restorative material, before, during, and after hardening, such that an oxygen inhibited layer can be maintained.

Figure 3:
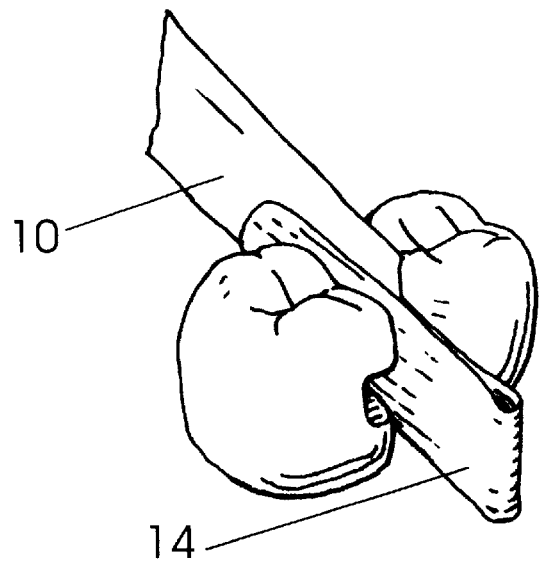
FIG. 3 shows a perspective view of a prepared tooth which has interproximal contact with an adjacent opposing tooth, with an inserted metal matrix strip covering a soft polymer matrix.

FIG. 3 shows a perspective view of a prepared tooth which has maintained interproximal contact with an adjacent opposing tooth, with an inserted folded metal matrix, metal matrix 14, which covers either side of strip 10. It is preferred that metal matrix 14 is dead soft, and 0.001 inch thick (SCHEIN). However, other matrices of the art can be effectively substitued for metal matrix 14.

Figure 4:
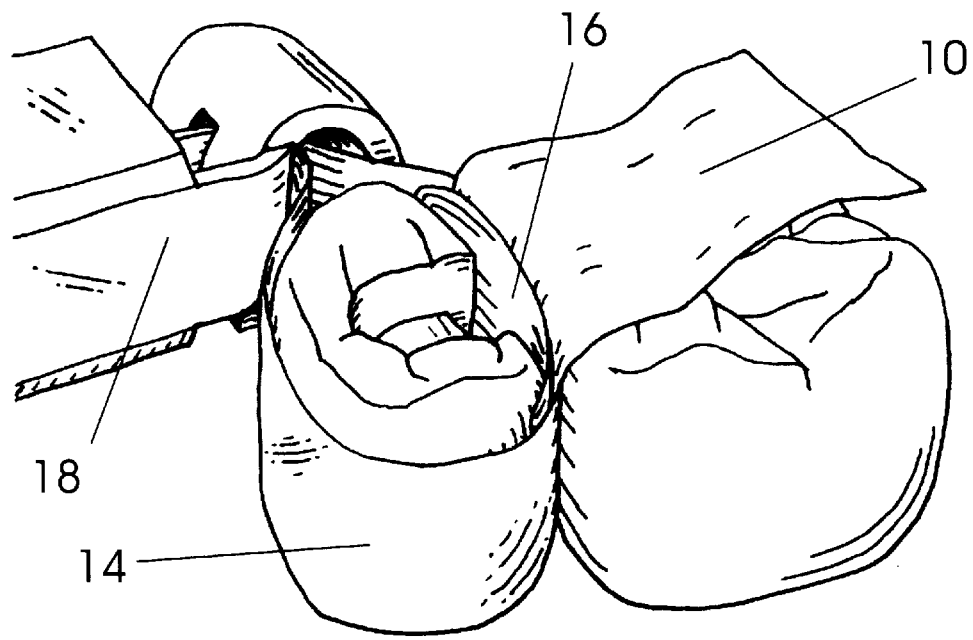
FIG. 4 shows a perspective view of a soft polymer matrix interposed between a prepared tooth and a metal matrix held by a retainer. A sectional matrix covers a portion of the soft polymer matrix.

FIG. 4 shows a perspective view of strip 10 interposed between a prepared tooth and metal matrix 14. Strip 10 covers the entire proximal surface a dental device, of metal matrix 14, opposing the preparation. The length of strip 10 is oriented gingival to occlusal with respect to the dental arch, over the interproximal area. The free end of strip 10 trails off over the opposing tooth. A sectional matrix, sectional matrix 16, is shown temporarily covering the interproximal portion of strip 10. Palodent Sectional Matrices (DARWAY, INC.) are preferred for sectional matrix 16. Metal matrix 14 is held under tension by a matrix band retainer, retainer 18, such as a Tofflemire retainer. However, other matrixing systems are adaptable for use with strip 10.

Figure 5:
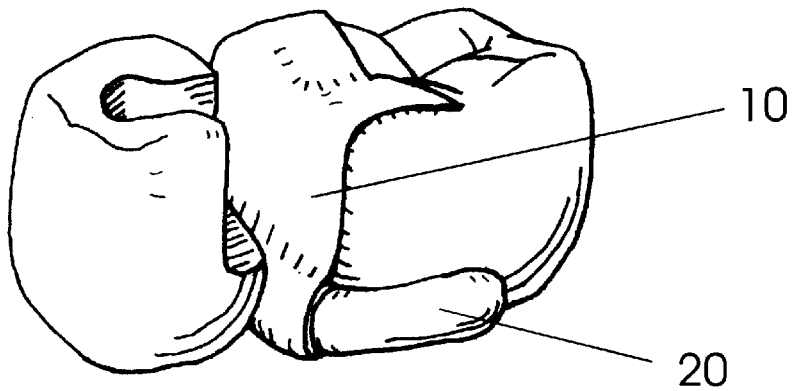
FIG. 5 shows a perspective view of a soft polymer matrix, partly spooled onto a blockout roll, covering the interproximal area of an adjacent opposing tooth.

FIG. 5 shows a perspective view of strip 10 covering an adjacent opposing tooth, with an interproximal blockout material, roll 20.

Roll 20 is comprised of a moldable mass for adaptation to blockout interproximal undercuts. Roll 20 functions as a shim to keep restorative materials, introduced later, out and away from interproximal undercut areas. In addition, roll 20 is moldable to form an interproximal matrix surface, to assist in molding restorative materials. The matrix surface of roll 20 extends from just below the interproximal contact area of the adjacent opposing tooth to the gingival margin of the prepared tooth.

The preferred roll 20 is comprised of an elongated cylinder, 4 cm in length, of dead soft polymer, such as could be made by gently spiral twisting a length of strip 10. However, other roll 20 materials which are effective include lengths of cylindrical soft polymer, such as PTFE, approximately 1 to 2 mm in diameter, multiple layers of PTFE tape, temporary or permanent composites, flowable composites, ionomers, resin ionomers, clay, wax, thermoplastic vinyls, impression materials, acrylics, denture liners, and so on.

As shown, one end of strip 10 has been rolled two to five, or more, times around roll 20, depending on the total volume of material required to fill the interproximal space. Either end of roll 20 is shown pulled back from the facial and lingual gingival margin areas of the prepared tooth, so as to be out of the way prior to loading restorative material.

Strip 10 is shown covering the adjacent opposing tooth. The length of strip 10 is oriented gingivally to occlusally with respect to the dental arch, as it covers the interproximal portion of the adjacent opposing tooth. The trailing end of strip 10 is shown pulled back and clinging to the occlusal surface of the adjacent opposing tooth, and the teeth beyond, prior to the final loading of hardenable restorative material into the prepared tooth.

Notably, there is no burnish 12 created on strip 10. The thickness of strip 10 is preserved to act as an intentional interproximal shim. The thickness of strip 10 shims restorative materials from the adjacent opposing tooth, during molding and hardening. When strip 10 is removed, pressure exerted by the restorative material against the adjacent opposing tooth is thereby somewhat decreased. This is preferred when elastomeric temporary restorative material is used. Otherwise, the elasticity of such temporary restorative materials tends to inadvertantly increase the distance between the prepared tooth and the adjacent opposing tooth.

Despite no burnish 12 being required on strip 10 for this process, strip 10 has sufficient other advantages for use in this process. Strip 10 closely spools around roll 20, without substantial tendency to unravel. Strip 10 enhances the moldability of roll 20, rather than diminishing it, as other plastic sheeting would. Strip 10 clings to the teeth and restorative material, so as to maintain positioning. Finally, strip 10 preserves the oxygen inhibited layer of the restorative material, which permits strong additions of restorative material, as needed.

Figure 6:
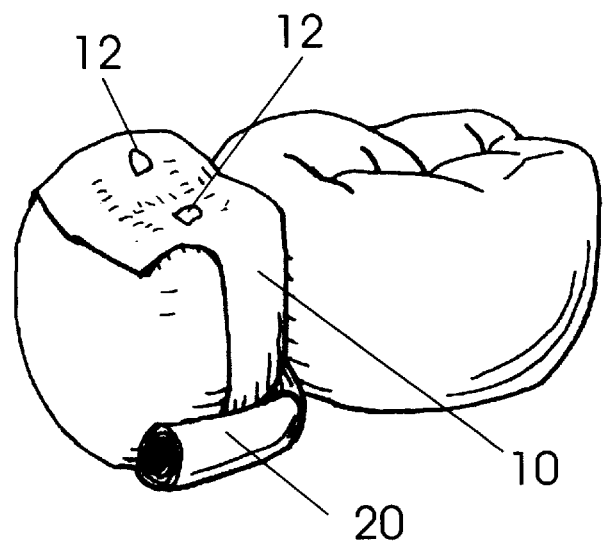
FIG. 6 shows a perspective view of a soft polymer matrix, with a blockout roll, covering hardenable restorative material in a prepared tooth.

FIG. 6 shows a perspective view of strip 10 and molded roll 20, covering hardenable restorative material in a prepared tooth. Roll 20 is against the respective facial and lingual surfaces of the prepared tooth. Strip 10 and roll 20 facilitate molding of the restorative material, and permit light hardening while preserving the oxygen inhibited layer.

Figure 7:
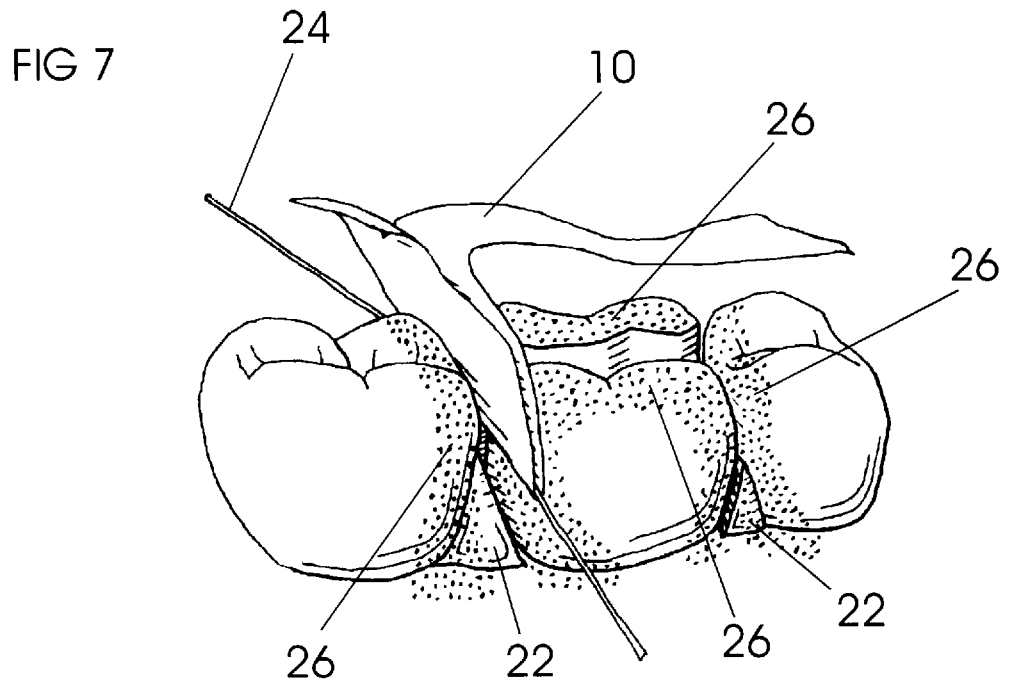
FIG. 7 shows perspective view of a soft polymer ready for introduction onto a prepared tooth, with an interproximal blockout placed in the interproximal areas, and adhesive selected surfaces of the teeth and gingiva.

FIG. 7 shows a perspective view of strip 10 being introduced onto the prepared tooth, with an interproximal blockout, blockout 22, in place. A length of dental floss, floss 24, is shown pulling a 25 mm wide strip 10 between the prepared tooth and blockout 22.

Blockout 22 is a material which occupies the interproximal undercuts formed by the adjacent opposing tooth. The preferred blockout 22 for this example of the process is comprised of hardenable material which may be injected through a syringe tip, such as light and chemical-curable Resinomer™ (BISCO). However, other blockout 22 materials which are effective include temporary or permanent composites, flowable composites, ionomers, resin ionomers, and so on. A temporary, orally compatible adhesive for use adhering strip 10 to dental surfaces, adhesive 26, is shown coated on surfaces of the prepared tooth, the adjacent teeth, including any dental restorations therein or thereon, and the gingiva. Adhesive 26 is orally compatible, and is capable of temporarily adhering a dead soft polymer, such as PTFE, to oral structures, dental restorative materials, dental restorations, and dental devices. Such adhesion of soft polymer is useful in procedures for dental matrixing, separation, positional stabilization of burnishable polymeric strips, and similar procedures related to the restoration of teeth. It is preferred that adhesive 25 is comprised of an emulsion of acrylic polymer and water, with a slight amount of ammonia. However, other orally compatible adhesives are effective.

Figure 8:
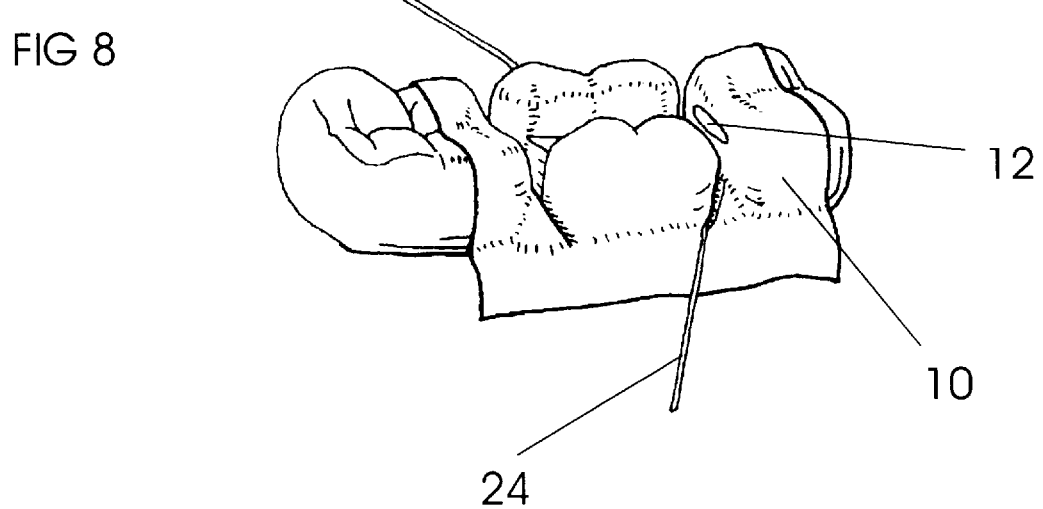
FIG. 8 shows a perspective view of a soft polymer strip mounted on a prepared tooth and over an interproximal blockout.

FIG. 8 shows a perspective view of strip 10 mounted over a prepared tooth, with blockout 22 placed in the interproximal areas. Strip 10 forms a matrix surface over the interproximal contact area, over blockout 22, and also over the prepared tooth surfaces. Strip 10 inhibits any introduced restorative material from flowing into small surface undercuts, or from adhering to prepared tooth surfaces.

From the description above, a number of advantages of my dead soft polymer strip become evident:

(a) Strip 10 permits formation of a restoration having ideal contact with the adjacent opposing tooth, without requiring the use of a wedge. This permits greater access to mold critical gingival margin areas, and reduces the likelihood of gingival bleeding from wedging.

(b) Strip 10 is readily burnishable to insubstantial thickness, so that it reduces the shimming of restorative material away from proper contact with an opposing tooth.

(c) Strip 10 is dead soft and adapts to the shape of, and clings to the surface of, the restorative material. Yet the clinging matrix strip provides some resistance to the relative movement of the surface particles of the moldable restorative material. As such, the restorative material is made somewhat resistant to inadvertent remolding, such as slumping, while permitting intentional remolding.

(d) Clinging strip 10 does not need to be held tightly about a prepared tooth to ensure good margins. As such, no bulky retainer is in the way, nor are fingers preoccupied with retaining the matrix.

(e) Strip 10 shapes restoration margins without overhangs. Strip 10 readily stretches flush over the preparation margins, and draws the restorative material along with it. Strip 10 then stabilizes the restorative material at the margins.

(f) Strip 10 substantially preserves the oxygen inhibited layer during the hardening of composite restorative materials. Micropores in strip 10 permit continuous contact of oxygen with the restorative material surface. Further, microscopic resin-tags are formed over the surface of the hardened restorative material. After removal of strip 10, further additions of restorative material can be bonded at nearly full strength to the available uncured resin.

(g) Strip 10 is not sharp or stiff, and so does not tend to cut the gingiva when placed to cover gingival margins.

When necessary, it can be stretched and pulled a substantial distance into the gingival sulcus to cover margins, without trauma to the gingiva.

(h) Strip 10 substantially absorbs bonding resins into its micropores. This facilitates limitation of resin movement more effectively than matrices of the art, and prevents resins from undesireably coating adjacent surfaces.

(i) Strip 10, adapted to the prepared tooth surfaces, will shim introduced restorative material away from the surfaces a small distance. If the preparation has a smooth surface with no obvious undercuts, the shimming distance will be adequate to keep the restorative material out of minor surface irregularities that could lock-in the restoration. Blockout 22, when adapted to blockout undercuts below the interproximal height of contour of the adjacent teeth, including under the interproximal contact area, will shim any introduced restorative material away from such undercut areas. The contact area itself can remain substantially unshimmed, with the insubstantial thickness of the burnish 12 area of strip 10, and still permit removal of the hardened restorative material.

(j) Strip 10 performs as an adequate separating layer between permanent restorative material, molded against substantially unshimmed interproximal contact areas, and the prepared tooth.

(k) When all available undercuts are blocked out with strip 10 and blockout 22, restorative material molded in the teeth against substantially unshimmed interproximal contact areas, may be hardened, and then removed without substantial deformation, fracture, or abrasion.

(l) When all available undercuts are blocked out with strip 10 and blockout 22, restorations molded in the teeth, by impression imprint, and against substantially unshimmed interproximal contact areas, may be hardened, and then removed without substantial deformation, fracture, or abrasion.

(m) Strip 10 provides adequate shimming separation of restorative materials from prepared tooth surfaces, and from basing and blockout materials on prepared tooth surfaces. Substantially hardened restorative material is inhibited from locking into minor surface undercuts, or from adhering to the prepared tooth surfaces, and is thereby consistently removable. Yet, the shimming separation is adequately minimal to ensure intimate adaptation of the restorative material to the prepared tooth surfaces, and to the opposing contact area.

(n) Most strip 10 processes eliminate the use of wedges by leaving the interproximal contact areas substantially unshimmed.

(o) Strip 10 affinity for resin restorative materials pulls them to its surface, and thereby promotes smooth restorative surfaces.

OPERATION—FIGS. 1 TO 8

By using the matrix strip of the invention, it is now possible, surprisingly, to rapidly and precisely mold complex restorative material shapes, and stabilize such shapes while hardening is completed, such that floss-snagging interproximal edges and overhangs are substantially eliminated. The process offers the advantage that the dental practitioner can now add restorative material to hardened, matrix-shaped surfaces, without substantial loss of bond strength. Further, the matrix strip may be released, once in position. With no required finger grip, retainer, or wedge to impede the molding process, the matrix covered restorative material can be freely molded to the desired shape.

The following example specifically illustrates a further embodiment of the present invention.

EXAMPLE 1

If a deficient anterior, or posterior, tooth has an interproximal deficiency, and the deficiency substantially includes the interproximal contact area, then the following procedure is preferred.

Implementation of the process begins with removing any plaque and calculus from a deficient anterior or posterior tooth and adjacent opposing teeth. The deficient tooth is prepared to form a prepared tooth, such that the prepared tooth loses any remaining interproximal contact area. Such tooth preparations range from minimal preparations to full crown preparations. There is no remaining substantial contact with the adjacent opposing tooth, and the interproximal space becomes open.

Restorative material is placed to partly fill the deeper areas of the tooth preparation. The prepared tooth is ready for insertion of the strip 10 when it is partly filled to within about 1 mm of the adjacent opposing tooth, and within about 0.5 mm of the interproximal margins.

An approximately 3 cm length of 12 mm wide dead soft polymer strip is cut from a supply spool, for use as strip 10. A similar length of standard 9 mm width, 0.002 inch thickness, mylar matrix (3M) is cut from a supply spool. The two lengths are superimposed over one another. As strip 10 is wider than the Mylar matrix, it will overhang slightly on either side. The lengths of the superimposed matrices are oriented facial to lingual, or buccal to lingual, over the prepared tooth. Hereinafter, facial surfaces or buccal surfaces of the teeth will be called facial.

The superimposed matrices are inserted into the open interproximal space between the prepared tooth and the adjacent opposing tooth. Care is taken keep the mylar matrix at or above the gingiva, to avoid trauma to the gingiva. The facial ends of the superimposed matrices are simultaneously pulled back and held against the facial surfaces of the adjacent opposing tooth, away from the prepared tooth. The lingual ends of the superimposed matrices are pulled back and held against the lingual surfaces of the adjacent opposing tooth.

An interproximal carver is firmly rubbed over the surface of the mylar matrix immediately over the interproximal contact area of the adjacent opposing tooth. The pressure from such rubbing deforms and burnishes strip 10, located immediately below the mylar matrix. As such, the thickness of strip 10 becomes insignificant over the interproximal contact area of the adjacent opposing tooth, to form burnish 12.

The ends of the mylar matrix and strip 10 are separated. Strip 10 is again held against the facial and lingual surfaces of the teeth. The mylar matrix is pulled free from the interproximal area. Strip 10 is smoothly pressed onto respective facial and lingual surface of the adjacent opposing tooth, and any teeth beyond. As such, strip 10 clings to the teeth, out of the way, as shown in FIG. 1.

Restorative material is added to approximate the final shape and color of the restoration. The facial and lingual ends of strip 10 are pulled free from the adjacent opposing tooth, and toward the respective facial and lingual surfaces of the prepared tooth. Care is taken to avoid displacing the restorative material away from the interproximal contact area. Care is also taken to avoid creating folds in strip 10. Strip 10 is smoothly adhered to the entire facial, lingual, and interproximal surfaces of the restorative material. The interproximal gingival edge of strip 10 is pulled and stretched to tuck subgingivally with an instrument, such as an interproximal carver, as necessary. Such pulling movement of strip 10 is accomplished by pinning strip 10 against tooth surfaces, then moving the instrument. Care is taken to avoid trauma to the gingiva. The overall contours of the restorative material are reshaped to approximate the final restoration contours.

The entire gingival margin area is feathered with light strokes of the interproximal carver or an explorer, moving from over the restorative material to the over the tooth surface until the restorative material is flush with the preparation margins, as shown in FIG. 2. In contrast to the art, relatively stiff and sharp matrices are not required to touch the interproximal gingiva, for is the strip 10 matrix retained in position by some retaining means.

Similarly to the art, for anterior tooth preparations which include the incisal edge, strip 10 will protrude above the incisal edge of the prepared tooth. As a result, restorative material must be permitted to temporarily extend above the final incisal edge contours, prior to hardening.

The restorative material is partly hardened, such as by transilluminating the restorative materials with a curing light through strip 10. Strip 10 is removed from the partly hardened restorative material. Any additional restorative material is added and contoured as necessary, even to matrix-shaped surfaces. The restorative material is completely hardened.

The interproximal contact area and the gingival margin are checked with multifiliment dental floss, to verify smoothness. The entire interproximal surface is typically free of overhangs and roughness, so that the floss does not snag. In contrast, restorations formed by processes of the art typically snag the floss, and require lengthy finishing procedures for the interproximal surfaces. The restoration surface receives final contouring and finishing, according to the art.

The following example specifically illustrates a further embodiment of the present invention.

EXAMPLE 2

If the deficient tooth has an interproximal deficiency, but the deficiency does not substantially include the actual interproximal contact area, then the following procedure is preferred. The deficient tooth is prepared to form a prepared tooth, such that the interproximal contact area between the prepared tooth and the adjacent opposing tooth is substantially preserved. Such tooth preparations range from minimal preparations to ⅞ crown preparations. As such, the interproximal space is partly closed. Dental floss is snapped through the interproximal contact. If the floss shreds, the contact is slightly smoothed, such as with a gapped sanding strip.

Preparation surfaces are further prepared for restorative materials, such as by etching and resin application. The resin is partly hardened, such as by illuminating with a curing lamp for about one fourth of the full resin cure time. The interproximal is flossed to clear excess resin. The resin is completely hardened, and flossed again.

Restorative material is placed to partly fill the deeper areas of the tooth preparation. The prepared tooth is ready for insertion of the strip 10 when it is partly filled to within about 1 mm of the adjacent opposing tooth, and within about 0.5 mm of the interproximal margins.

An approximately 4 cm length of 12 mm wide dead soft polymer strip is cut from a supply spool, for use as strip 10. The length of strip 10 is aligned with the length of metal matrix 14. Strip 10 is laid over metal matrix 14, such that half of the length of strip 10 is on metal matrix 14, the other half of strip 10 extends beyond an end of metal matrix 14, and a lateral edge of strip 10 is flush with a lateral edge of metal matrix 14. The opposite lateral edge of strip 10 will extend beyond the corresponding opposite lateral edge of metal matrix 14.

Metal Matrix 14 with strip 10 is oriented facially to lingually over the interproximal contact area adjacent to the preparation, such that the strip 10 covered portion of metal matrix 14 is toward the lingual, and the lateral edge of strip 10 which is flush with metal matrix 14 is toward the gingiva.

The facial, uncovered portion of metal matrix 14 is folded over strip 10 such that the ends of metal matrix 14 are offset from one another by 3 mm, one portion being longer, and one portion being shorter, with the longer portion adjacent to the prepared tooth. The shorter portion of metal matrix 14 is adjacent to the adjacent opposing tooth. Strip 10 is sandwiched between the potions of the folded metal matrix. Approximately half of strip 10 will remain protruding beyond the offset ends of folded metal matrix 14, and half will be covered on either side by folded metal matrix 14. The fold-end of metal matrix 14 is toward the facial, and the offset ends of metal matrix 14 are toward the lingual. This forms an offset sandwiched strip 10.

Offset sandwiched strip 10 is positioned such that two-thirds of the length of the folded metal matrix is facial to the interproximal contact area, and one-third is to the lingual. Sandwiched strip 10 is inserted through the interproximal contact, between the prepared tooth and the adjacent opposing tooth. Sandwiched strip 10 is inserted sufficiently to cover just beyond the gingival margin of the preparation, as shown in FIG. 3.

The facial portion of sandwiched strip 10 is grasped and pulled toward the facial, until the shorter portion of metal matrix 14 is free of the interproximal contact area. The longer portion of metal matrix 14 remains in the interproximal contact area. An interproximal carver instrument is rubbed firmly over the surface of metal matrix 14 over the interproximal contact area, pressing toward strip 10 and the adjacent opposing tooth. This forms burnish 12 on strip 10.

The facial and lingual ends of strip 10 are pulled back toward, pressed onto, and held against, the respective facial and lingual surfaces of the adjacent opposing tooth. Metal Matrix 14 is pulled free of the interproximal area. The ends of strip 10 remain pressed onto the surfaces of the adjacent opposing tooth, out of the way.

As in the previous example, restorative material is added and molded to approximate final restoration contours. The ends of strip 10 are pulled to smoothly cover the restorative material and the prepared tooth. Strip 10 is stretched where necessary to cover the preparation margins. The restorative material is further molded, especially feathering margins. The restorative material is hardened, to form a restoration. Strip 10 is removed. The restoration receives final hardening and finishing, as in the art.

The following example specifically illustrates a further embodiment of the present invention.

EXAMPLE 3

If a deficient tooth has an interproximal deficiency, but the deficiency does not substantially include the actual interproximal contact area, and the adjacent opposing tooth is similarly deficient, then the following procedure is preferred.

The deficient teeth are both prepared to form a first preparation in a first prepared tooth, and an opposing second preparation in an opposing second prepared tooth, such that the interproximal contact area between the prepared teeth is substantially preserved. As such, the interproximal space is partly closed. Dental floss is snapped through the interproximal contact. If the floss shreds, the contact is slightly smoothed, such as with a gapped sanding strip.

Both the first and second prepared teeth are further prepared for restorative materials, such as by simultaneous etching, rinsing, and resin application. The resin is partly hardened, such as by illuminating with a curing lamp for about one fourth of the full resin cure time. The interproximal is flossed to clear excess resin. The resin is completely hardened, and flossed again.

Restorative material is placed to partly fill both opposing preparations to within about 1 mm of the final restoration contours. As such, about 2 mm separates the restorative material in the first preparation from the restorative material in the second preparation. Restorative material is also kept about 0.5 mm from interproximal margins.

An approximately 3 cm length of 12 mm wide dead soft polymer strip is cut from a supply spool, for use as strip 10. The length of strip 10 is aligned with metal matrix 14. Strip 10 is laid over metal matrix 14, such that half of the length of strip 10 is on metal matrix 14, the other half of strip 10 extends beyond an end of metal matrix 14, and a lateral edge of strip 10 is flush with a lateral edge of metal matrix 14. The opposite lateral edge of strip 10 will extend beyond the opposite lateral edge of metal matrix 14. Metal Matrix 14 is folded in half over strip 10, such that half the length of strip 10 is sandwiched between the halves of metal matrix 14. It is not necessary to offset the ends of metal matrix 14. The remaining half of strip 10 protrudes beyond the length of the folded metal matrix. This forms a sandwiched strip 10.

Sandwiched strip 10 is positioned such that two-thirds of the length of the folded metal matrix is facial to the interproximal contact area, and one-third is to the lingual. Sandwiched strip 10 is inserted through the interproximal contact, between the prepared tooth and the adjacent opposing tooth. Sandwiched strip 10 is inserted sufficiently to cover just beyond the gingival margin of the preparation, as shown in FIG. 3.

The facial portion of sandwiched strip 10 is grasped and pulled toward the facial, until metal matrix 14 is free of the interproximal contact area. Metal Matrix 14 is teased free of strip 10, with minimal disturbance of strip 10, and set aside. The facial and lingual ends of strip 10 are pulled back toward, and pressed against, the respective facial and lingual surfaces of the opposing second prepared tooth.

Restorative material is added and molded to approximate final restoration contours in the first preparation. Strip 10 is smoothly pulled over to cover the restorative material and the first preparation margins, stretching strip 10 when necessary. The restorative material is further molded, as necessary, especially feathering margins. The restorative material is hardened, to form a first restoration.

Burnish 12 may be created on strip 10 if it is desirable to enlarge the interproximal contact area which already exists between the prepared teeth. One way to create burnish 12 is to cut a metal matrix so as to leave a curved protrusion which is sufficiently small to fit into the second preparation, and large enough to cover the interproximal contact area of the first restoration. The metal matrix protrusion is placed over the strip 10-covered contact area of the first restoration. A hand instrument, such as an interproximal carver is rubbed firmly over the surface of the metal matrix protrusion to create burnish 12 on strip 10.

Restorative material is added and molded to approximate final restoration contours in the second preparation. Strip 10 is smoothly pulled over to cover the restorative material and the second preparation margins, stretching strip 10 when necessary. The restorative material is further molded, as necessary, especially feathering margins. The restorative material is hardened, to form a second restoration. Strip 10 is removed. The first and second restorations receive final hardening and finishing, as in the art.

The following example specifically illustrates a further embodiment of the present invention.

EXAMPLE 4

Implementation of the process begins with removing any plaque and calculus from a posterior tooth with an interproximal deficiency which substantially includes the interproximal contact area, and from the adjacent opposing teeth. The deficient tooth is prepared to form a prepared tooth, such that the prepared tooth loses any remaining interproximal contact area. There is no substantial contact with the adjacent opposing tooth, and the interproximal space becomes open.

Metal matrix 14 is mounted in retainer 18, such that it forms a loop for encompassing a tooth. However, other matrixing systems of the art may be substituted for metal matrix 14 or retainer 18, such as sectional matrix systems. The gingival edge portion of metal matrix 14, which will be adjacent to the preparation gingival margin when metal matrix 14 is mounted on the prepared tooth, is located. About 1 mm of said gingival edge portion of metal matrix 14 is coated on either side with adhesive 26.

An approximately 3 cm length of 12 mm wide dead soft polymer strip is cut from a supply spool, for use as strip 10. Cotton pliers are used to place one end of strip 10 into the metal matrix 14 loop, such that the strip 10 end protrudes beyond the adhesive 26 coated metal matrix 14 edge about 1 mm. Strip 10 is smoothly placed on the adhesive 26 coated edge. The end of strip 10 which protrudes beyond the metal band 1 mm is wrapped back onto the outer surface of metal matrix 14, which was coated with the adhesive 26. The wrapped back end of strip 10 is smoothly adhered to metal matrix 14. The other, non-adhered end of strip 10 trails freely out the occlusal edge of the metal matrix 14 loop.

Metal matrix 14, with retainer 18 and adhered strip 10, is placed on the prepared tooth such that the edge of metal matrix 14, upon which strip 10 is adhered, is immediately gingival to the gingival margin of the preparation. Retainer 18 is tightened to lightly cinch metal matrix 14 around the tooth.

Strip 10 is pulled slightly to create tension while sectional matrix 16 is inserted between the gingival margin of the preparation and strip 10. The tension prevents strip 10 from being transported gingivally during the insertion of sectional matrix 16. The trailing end of strip 10 is laid over the occlusal surface of the adjacent opposing tooth, as shown in FIG. 4.

A wedge of ideal shape is placed interproximally to move the matrices against the gingival margin, but at reduced pressure. Reduced wedge pressure reduces the chance of gingival bleeding at this step. Burnish 12 is created on strip 10 by pressing and rubbing a ball burnisher against the portion of sectional matrix 16 which overlies the interproximal contact area, to cause strip 10 to have insubstantial thickness over the contact area.

The preparation is etched and rinsed. Dentin and enamel bonding resins are applied. Sectional matrix 16 somewhat restricts the flow of the bonding resins from contacting, and being absorbed into, the micropores of strip 10. Sectional matrix 16 is removed without disturbing strip 10. Retainer 18 is tightened to full tension. The wedge is pressed interproximally to normal pressure.

A condensable, autocuring restorative material, such as Bisfil II™ (BISCO), is placed to partly fill the deeper areas of the tooth preparation, and up to and including the interproximal contact area. Before the restorative material hardens, the tension on retainer 18 is relaxed slightly. Strip 10 is laid closely over the restorative material. As the restorative material just begins to harden, pressure is applied to the strip 10 covered restorative material surface, such as with a condenser, angled toward the interproximal contact area. Pressure is maintained until the restorative material is hardened. Strip 10 is lifted from the surface of the hardened restorative material, and laid over the adjacent opposing tooth.

Resin is applied to the occlusal surface of the hardened restorative material. Unhardened restorative material, such as light curable composite, is added to the hardened restorative material, and molded to approximate final restoration contours. Strip 10 is smoothly pulled over to cover the unhardened restorative material. The marginal ridge area of the unhardened restorative material is further molded to an ideal shape, free of sharp edges. This is in contrast with the art, in which restorative materials form a sharp edge against the surface of metal matrix 14.

The restorative material is hardened, such as by transmitting a curing light through strip 10. Strip 10 is removed. The restorative material is further hardened. In contrast to the art, dental floss will generally pass through the interproximal contact area without significant snagging on sharp edges of restorative material. When such sharp edges are present, tedious finishing procedures are required to eliminate them. The restorative material receives final hardening and finishing, to form a restoration.

The following example specifically illustrates a further embodiment of the present invention.

EXAMPLE 5

Implementation of the process begins with removing any plaque and calculus from a posterior tooth with an interproximal deficiency which substantially includes the interproximal contact area, and from the adjacent opposing teeth. The deficient tooth is prepared to form a prepared tooth, such that the prepared tooth loses any remaining interproximal contact area. There is no substantial contact with the adjacent opposing tooth, and the interproximal space becomes open. Metal matrix 14 is mounted in retainer 18, such that it forms a loop for encompassing a tooth. The gingival edge portion of metal matrix 14, which will be adjacent to the preparation gingival margin when metal matrix 14 is mounted on the prepared tooth, is located. About 1 mm of said gingival edge portion of metal matrix 14 is coated on either side with adhesive 26.

An approximately 3 cm length of 12 mm wide strip 10 material tape is cut from a supply spool, for use as strip 10. Cotton pliers are used to place one end of strip 10 into the metal matrix 14 loop, such that the strip 10 end protrudes beyond the adhesive 26 coated metal matrix 14 edge about 1 mm. Strip 10 is smoothly placed on the adhesive 26 coated edge. The end of strip 10 which protrudes beyond the metal band 1 mm is wrapped back onto the outer surface of metal matrix 14, which was coated with adhesive 26. The wrapped back end of strip 10 is smoothly adhered to metal matrix 14. The other, non-adhered end of strip 10 trails freely out the occlusal edge of the metal matrix 14 loop. However, other porous materials may be placed to cover metal matrix 14.

Metal matrix 14, with retainer 18 and adhered strip 10, is placed on the prepared tooth such that the edge portion of the metal band with strip 10 adhered is immediately gingival to the gingival margin of the preparation. Optionally, a sectional matrix 16 can be temporarily inserted between strip 10 and the preparation, as an additional restrictive matrix surface to limit the flow of bonding resins, as shown in FIG. 4. However, strip 10 is substantially effective without sectional matrix 16.

Retainer 18 is lightly cinched around the tooth. A wedge of ideal shape is placed interproximally to move the matrices against the gingival margin, but not at full pressure. Reduced wedge pressure reduces the chance of gingival bleeding at this step.

The preparation is etched and rinsed. Dentin and enamel bonding resins are applied, such as Amalgambond™ (PARKELL). Strip 10 substantially restricts the flowable bonding resins from coating metal matrix 14. Strip 10 acts as a matrix by presenting a limiting surface to restrict the location of the resins, but also absorbs excess resin into its micropores. The unique absorption process of strip 10 substantially inhibits the flow of the resins around strip 10. If a sectional matrix 16 were used without strip 10, a substantial resin film would appear on the surface of metal matrix 14. Retainer 18 is held in its position while resin-soaked strip 10 is pulled away, along with sectional matrix 16, if present.

Retainer 18 is tightened to full tension. The wedge is pressed interproximally to normal pressure. Restorative material, such as dental amalgam, is placed and finished, according to the art.

The following example specifically illustrates a further embodiment of the present invention.

EXAMPLE 6

Implementation of the process begins with removing any plaque and calculus from a deficient tooth and adjacent opposing teeth. The deficient tooth has a deficiency in the interproximal area, adjacent to an adjacent opposing tooth. The deficiency substantially includes the interproximal contact area, which is in direct contact with the adjacent opposing tooth.

The deficient tooth is prepared to form a prepared tooth. As such, the prepared tooth loses the interproximal contact area with the adjacent opposing tooth. The interproximal space becomes substantially open.

An approximately 4 cm length of 12 mm width dead soft polymer strip is cut from a supply spool. The strip is twisted such that a cylindrical roll is formed, with a diameter of approximately 1 mm, to form roll 20. An approximately 3 cm length of 12 mm width soft polymer strip is cut for use as strip 10. The length of strip 10 is oriented perpendicularly to the length of roll 20. Strip 10 is spooled around the center area of the length of the roll 20 cylinder for 2 or more turns. Each additional turn of strip 10 around roll 20 effectively increases the total diameter of roll 20. For smaller interproximal spaces, use 2 to 3 turns. For larger interproximal spaces, use 4 or more turns.

Roll 20, with spooled strip 10, is placed into the interproximal space between the prepared tooth and the adjacent opposing tooth, such that the length of roll 20 is parallel to, and adjacent to, the interproximal gingival margin of the tooth preparation. The free end of strip 10 trails occlusally, away from the gingiva. Strip 10 is temporarily laid back along the occlusal surface of the adjacent opposing tooth, out of the way. The interproximal portion of roll 20 is pressed into the interproximal space between the gingival margin of the tooth preparation and the adjacent opposing tooth.

Roll 20 is molded with hand instruments such that it substantially covers the interproximal gingival papilla, and occupies the portion of the interproximal space which is not intended to be occupied by the restoration. Roll 20 is feathered thin as it approaches the interproximal contact area of the adjacent opposing tooth, such that only strip 10 covers the contact area. Roll 20 is molded such that it does not overhang the interproximal preparation margin. The free end portion of roll 20 which protrudes to the lingual is pressed back along the lingual surfaces of the adjacent opposing tooth, out of the way. The free end portion of roll 20 which protrudes to the facial is pressed back along the facial surfaces of the adjacent opposing tooth, as shown in FIG. 5.

Hardenable restorative material, such as temporary restorative material, is loaded into the tooth preparation. The restorative material is molded to substantially restore the deficient tooth to it's ideal shape. Strip 10 is pulled to cover the occlusal surface of the restorative material. Care is taken not to pull the restorative material away from the interproximal contact area. The facial and lingual ends of roll 20 are pulled alongside the respective facial and lingual surfaces of the prepared tooth. The hardenable restorative material receives additional contouring through strip 10 and roll 20.

The patient occludes the teeth together firmly. The occlusal contacts create burnish 12 deformations on the occlusal portion of strip 10, which permits substantially unshimmed occlusion of the teeth. However, strip 10 shims hardenable restorative material slightly away from the opposing occluding teeth. This reduces the incidence of hyperoccluded restorative material. The restorative material is hardened, such as by transmitting a curing light through strip 10 from the facial of the occluded teeth. The patient opens, and the occlusal and lingual surfaces are hardened, as shown in FIG. 6. Strip 10 is pulled back from the hardened restorative material. Further hardening is performed, such as by direct exposure to a curing light.

Strip 10 and roll 20 are pulled from the teeth and discarded. The restorative material receives final hardening and finishing, as in the art.

The following example specifically illustrates a further embodiment of the present invention.

EXAMPLE 7

Implementation of the process begins with removing any plaque and calculus from a deficient tooth and adjacent opposing teeth. The gingival health must be assessed as optimal. The deficient tooth has a deficiency in the mesial and distal interproximal areas, adjacent to adjacent opposing teeth. The deficiency substantially includes the interproximal contact areas, which are in direct contact with the adjacent opposing teeth. The deficiency is of sufficient proportions that the restorative material is to be formed in the tooth, then removed from the tooth for laboratory processing, such as strengthening or hardening, prior to cementation in the tooth. Tooth preparations range from moderate sized preparations to full crown preparations.

The restoration tooth is temporarily repaired to its original shape with temporary composite, permanent composite, clay, or such. An impression imprint of the tooth is taken with clear impression material, such as translucent polyvinylsiloxane PolySil® TransBite (SCI CAN). Clear impression trays are used, such as Perforated Clear Quadrant Impression Trays, No. I1T or No. I2T (CROSS TEX). Impression material in interproximal areas should be removed with a #15 scalpel blade (BARD-PARKER) to permit reseating later.

The deficient tooth surfaces are prepared in the usual divergent manner, to form a prepared tooth, such that the prepared tooth loses any remaining interproximal contact areas. There is no substantial contact with the adjacent opposing teeth, and the interproximal spaces become open. The opposing interproximal contact areas are resurfaced to ensure polished, undercut free, parallel or slightly divergent, planes that do not overhang the preparation gingival margin.

Separating wax is applied to the outer surface of metal matrix 14. Metal matrix 14, with retainer 18 and gentle wedging, is placed on the prepared tooth. Bleeding must not be initiated. The preparation is etched, rinsed, and bonded according to the art. Restorative material, such as Æliteflo™ (BISCO), is applied to internal line angles, undercuts, and gingival margins, and hardened. However, it is also effective to be applied to cover all internal preparation surfaces with restorative material. Restorative material is hardened, and the wedging is removed. Metal matrix 14 remains in place.

The interproximal spaces adjacent to the prepared tooth are syringe-filled with blockout 22 material, such as Resinomer™ (BISCO). However, for very large interproximal spaces, a weaker blockout 22 material is used, such as Fermit-N (Ivoclar). Pressure is applied to metal matrix 14 over the interproximal contact areas, such as with a hand instrument, to exclude blockout 22 from the interproximal contact areas. Blockout 22 is hardened, such as by exposure to a curing light. Metal matrix 14 is removed such that blockout 22 is not loosened. If blockout 22 loosens, lightly etch the tooth surfaces prior to replacement.

The position formerly occupied by metal matrix 14 is now a narrow slit between the prepared tooth and blockout 22. The contact areas of the adjacent opposing teeth are cleared of any extraneous blockout 22, such as by polishing with Soflex™ discs (3M). Any blockout 22 polishing debris is removed from the surface of the restorative material in the preparation, such as by brushing with All-Bond Resin™ (BISCO), followed by air thinning.

A thin coat of flowable restorative material, such as dual-cure Bisfil™ 2B (BISCO), is applied to the restorative material in the preparation, and left uncured. This provides an adhesive surface within the preparation area for strip 10.

An approximately 5 cm length of 25 mm wide strip 10 material is cut from a supply spool. Floss 24 is laid perpendicularly across the length of strip 10, at about 2 cm from one end of strip 10. The 2 cm end is folded back on itself, over floss 24. Floss 24 is positioned over the distal interproximal space, such that the 2 cm end of strip 10 is toward the distal adjacent opposing tooth, and the remaining 3 cm end is toward the prepared tooth. Strip 10 is introduced by driving the strip 10 fold into the interproximal space to the gingiva via floss 24. Floss 24 and strip 10 are negotiated through the narrow slit remaining between the prepared tooth and blockout 22, said narrow slit being created by metal matrix 14, as shown in FIG. 7. It is preferable to pull strip 10 slightly subgingival with floss 24. Floss 24 is removed by pulling it out toward the facial. An interproximal carver is used to ensure adaptation of strip 10 into the slit.

Using a Microbrush™ (SCHEIN), strip 10 is smoothly adapted to the prepared tooth surfaces. Care is taken to avoid folds in strip 10. Strip 10 is adapted down onto the interproximal surfaces, then onto tooth preparation surfaces coated with uncured, dual-curable restorative material. Strip 10 is adapted onto the second interproximal area, when present, using floss and the interproximal carver.

Adhesive 26 is lightly applied to the surrounding non-prepared tooth surfaces, including the adjacent opposing teeth, restorations of the teeth, and the gingiva, to provide an adhesive surface for strip 10. However, adhesive 26 may be applied prior to the introduction of strip 10. It is lightly air dried until tacky. The extremities of strip 10 are adapted and adhered to the adhesive coated surfaces. The restorative material under strip 10 is hardened, such as by exposure with a light.

A mylar matrix strip is positioned over the distal interproximal contact area. A hand instrument is rubbed over the matrix strip at the interproximal contact area to create a burnish 12. Burnish 12 is similarly created at the mesial interproximal contact area, as shown in FIG. 8.

A thin layer of viscous, flowable restorative material, such as Flow-It Lf™ (JENERIC-PENTRON), or a flowable restorative materials with etchable glass phase, is applied to internal preparation and interproximal surfaces of strip 10, and hardened. This prevents adhesion to resins through strip 10. Another layer of material, such as dual-curable Bisfil™ 2B (BISCO), is applied over the hardened restorative material in the preparation, and left uncured.

An adequate amount of restorative material, such as light-curable Charisma (KULZER), is loaded in the areas of the impression imprint which correspond to the tooth preparation. The imprint, with loaded restorative material, is seated over the prepared tooth. The imprint is fully seated, such as by pressure, sonic vibration, or other means, to displace excess restorative material. The restorative material is hardened, such as by transmitting sufficient curing light through the translucent imprint. The imprint is removed from the teeth.

Remove blockout 22 with a hand instrument. Remove flashing of excess restorative material. Remove hardened restorative material from tooth preparation, such as by gathering all edges of strip 10 together, and lifting. Further removal procedures include using dental floss to remove strip 10 from the interproximal contact areas. Thread dental floss under interproximal contacts. Lift the dental floss, under the restorative material, with moderate force, or pry at the restorative material, until it is freed from the tooth. Remove strip 10 from the hardened restorative material.

The substantially hardened restorative material is fitted to the prepared tooth. The restorative material is reseated in the tooth preparation to check the fit. In contrast to the procedures of the art, such reseating is typically immediate. If the material was taken out of the tooth, it will readily seat back into the tooth. However, if the restorative material does not seat, cover the interfering portion of the restorative material with a length of soft polymer strip, such as strip 10, wherein the position of the strip is stabilized by an adhesive 26 coating on the restorative material. Visually check for pressure burnishes on the strip prior to recontouring, as in the art. Once fitted, the substantially hardened restorative material is known as a substantially hardened restoration.

The substantially hardened restoration is subjected to complete hardening processes known to the art, such as timed exposure to heat and light in a laboratory, to form a completely hardened restoration. The completely hardened restoration is rechecked for fit, etched as necessary, bonded, cemented, such as with Sono Cem™ (ESPE), and surface finished, all according to the art. This completes the restorative process.

SUMMARY, RAMIFICATIONS AND SCOPE

Accordingly, the reader will see that the dead soft polymer strip of this invention permits rapid matrix molding of restorative material with a substantial reduction in the formation of overhanging margins. Furthermore, the dead soft polymer strip and processes have the additional advantages in that they permit strong additions of restorative material to restorative surfaces previously molded under the matrix strip.

Although the description above contains many specificities, these should not be construed as limiting the scope of the invention and process, but as merely providing illustrations of some of the presently preferred embodiments of this invention. For example, blockout 22 can be formed by injecting hardenable material into the interproximal area prior to preparing the tooth, rather than after. The material is hardened to record the interproximal contours of the deficient tooth, such as prior to the removal of an old amalgam restoration, to form blockout 22.

As a second example, strip 10 may be used as a matrix for placing restorative materials into subgingival restorations. The restorative material is placed to fill the preparation. Strip 10 is placed to cover the supergingival restorative material. The gingival edge of strip 10 is then pushed into the sulcus, below the gingival margin of the preparation, such as with an interproximal carver. The action is similar to that of packing gingival retraction cord. The restorative material is shaped to become flush with the preparation margin. The restorative material is hardened through strip 10. Strip 10 is removed, and the restoration receives final hardening and polishing.

As a third example, strip 10 may be used as an occlusion molding matrix, such as for restorations with a large occlusal surface such as for the restoration of Operation, example 7, in lieu of molding the occlusal surface with an impression. After placing the layer of restorative material which will be in occlusion with the opposing dentition, a 25 mm wide strip 10 is placed to cover and seal the restorative material. The patient occludes the teeth over strip 10. The patient opens the mouth for inspection of the occlusal imprint into the restorative material. If the restorative material requires remolding, strip 10 is removed, and remolding is performed. Strip 10 is replaced. The patient occludes the teeth over strip 10, to imprint the restorative material, and opens for inspection. If the imprint is satisfactory, the patient again grinds the teeth, and hardening of the restorative material is initiated, such as by directing a curing light from the facial. The patient opens the mouth, and hardening is completed. Strip 10 is removed from the hardened restorative material. The restorative material receives final contouring and polishing.

As a fourth example, when restoring a tooth with substantially preserved interproximal contact, burnish 12 may alternatively be created by making a sandwiched strip 10, with the ends of folded metal matrix 14 being even. Sandwiched strip 10 is inserted into the interproximal area. Sandwiched strip 10 is then grasped and moved in a circular pattern, so as to permit the pressure of the existing interproximal contact to burnish strip 10. Metal matrix 14 is teased away from strip 10, and removed one side at a time, while strip 10 is anchored by finger pressure. As a fifth example, temporary or permanent restorative material may be entirely enclosed within strip 10, placed into a prepared tooth, molded, hardened, and removed for laboratory processing.

Thus the scope of the invention should be determined by the appended claims and their legal equivalents, rather than by the examples given.

I claim:

1. A process for restoring a deficient tooth with a hardenable dental restorative material, wherein the deficiency of said deficient tooth includes an interproximal surface of said deficient tooth, said interproximal surface being adjacent to an adjacent opposing tooth, said process comprising the steps of:

preparing said deficient tooth to form a prepared tooth;
   introducing said hardenable restorative material onto said prepared tooth;
   introducing a length of dead soft polymer strip to cover said hardenable restorative material, said strip having cross-sectional dimensions which remains substantially constant throughout the length of said strip, wherein at least a portion of said strip is interposed between said adjacent opposing tooth and said hardenable restorative material;
   molding said hardenable restorative material, including molding said hardenable restorative material by manipulation of said strip;
   hardening said hardenable dental restorative material to form hardened restorative material;
   removing said strip from said hardened restorative material;
   finishing surfaces of said hardened restorative material to form a hardened restoration.

2. The process according to claim 1, wherein said polymer strip is comprised substantially of PTFE.

3. The process according to claim 1, wherein a dental matrix is interposed between said strip and said adjacent opposing tooth.

4. A process for restoring a deficient tooth with a hardenable dental restorative material, said process comprising the steps of:

preparing said deficient tooth to form a prepared tooth;
   introducing said hardenable restorative material onto said prepared tooth;
   introducing a length of dead soft polymer strip to cover said hardenable restorative material, said strip having cross-sectional dimensions which remains substantially constant throughout the length of said strip;
   molding said hardenable restorative material, including molding said hardenable restorative material by manipulation of said strip;
   hardening said hardenable dental restorative material to form hardened restorative material;
   removing said strip from said hardened restorative material;
   finishing surfaces of said hardened restorative material to form a hardened restoration.

5. The process according to claim 4, wherein said polymer strip is comprised substantially of PTFE.

6. A process for restoring a deficient tooth with a hardenable dental restorative material, wherein the deficiency of said deficient tooth includes an interproximal surface of said deficient tooth, said interproximal surface being adjacent to an adjacent opposing tooth, said process comprising the steps of:

preparing said deficient tooth to form a prepared tooth;
   introducing said hardenable restorative material onto said prepared tooth;
   introducing a length of dead soft polymer strip to cover said hardenable restorative material, said strip having cross-sectional dimensions which remains substantially constant throughout the length of said strip, said strip being comprised substantially of PTFE, wherein at least a portion of said strip is interposed between said adjacent opposing tooth and said hardenable restorative material;
   molding said hardenable restorative material, including molding said hardenable restorative material by manipulation of said strip;
   hardening said hardenable dental restorative material to form hardened restorative material;
   removing said strip from said hardened restorative material;
   finishing surfaces of said hardened restorative material to form a hardened restoration.

7. The process according to claim 6, wherein a dental matrix is interposed between said strip and said adjacent opposing tooth.

8. A process for restoring a deficient tooth with a hardenable dental restorative material, said process comprising the steps of:

preparing said deficient tooth to form a prepared tooth;
   introducing said hardenable restorative material onto said prepared tooth;
   introducing a length of dead soft polymer strip to cover said hardenable restorative material, said strip having cross-sectional dimensions which remains substantially constant throughout the length of said strip, wherein said strip is comprised substantially of PTFE;
   molding said hardenable restorative material, including molding said hardenable restorative material by manipulation of said strip;
   hardening said hardenable dental restorative material to form hardened restorative material;
   removing said strip from said hardened restorative material;
   finishing surfaces of said hardened restorative material to form a hardened restoration.

9. A process for forming a hardened restoration in a prepared tooth with a hardenable dental restorative material, said process comprising the steps of:

preparing a deficient tooth to form a prepared tooth, such that said prepared tooth has prepared surfaces of said prepared tooth;
   introducing a length of dead soft polymer strip to cover at least a portion of said prepared surfaces of said prepared tooth, wherein said strip is comprised substantially of PTFE;
   introducing said hardenable restorative material onto at least a portion of said polymer strip;
   molding said hardenable restorative material;
   hardening said hardenable dental restorative material to form hardened restorative material;
   removing said hardened restorative material from said polymer strip, removing said hardened restorative material from said prepared surfaces of said prepared tooth, and removing said polymer strip from said prepared surfaces of said prepared tooth;
   fitting and finishing surfaces of said hardened restorative material to form a hardened restoration.

10. The process according to claim 9, wherein said hardenable restorative material is a composite.

11. The process according to claim 9, wherein said hardenable restorative material is a temporary restorative material.

12. The process according to claim 9, wherein said polymer strip covers at least a portion of an adjacent surface of said adjacent opposing tooth.

13. The process according to claim 9, wherein said polymer strip covers at least a portion of said hardenable restorative material.

14. A process for restoring a deficient tooth with a hardenable dental restorative material, said process comprising the steps of:

preparing a deficient tooth to form a prepared tooth, such that said prepared tooth has prepared surfaces of said prepared tooth;

introducing a substantially porous material to cover a surface adjacent to said prepared surfaces of said prepared tooth;

introducing a dental restorative resin onto said prepared surfaces of said prepared tooth, such that said porous material absorbs excess said dental restorative resin, and said surface adjacent to said prepared surfaces of said prepared tooth remains substantially free of excess said dental restorative resin;

removing said porous material from said surface adjacent to said prepared surfaces of said prepared tooth;

restoring said deficient tooth with said hardenable dental restorative material.

15. The process according to claim 14, wherein said surface adjacent to said prepared surfaces of said prepared tooth is a dental matrix.

16. The process according to claim 14, wherein said porous material is comprised substantially of PTFE.

17. A process for removably affixing a dead soft polymer strip to a dental surface, said dental surface including surfaces of teeth, restorations of teeth, restorative material, gingiva, or dental devices, said process comprising the steps of:

coating said dental surface with an intraorally compatible temporary adhesive to form an adhesive dental surface;

mounting said strip onto said adhesive dental surface, such that said strip substantially covers said adhesive dental surface, and such that said strip removably adheres to said adhesive dental surface.

18. A process for removably affixing a dead soft PTFE strip to a dental surface, said dental surface including surfaces of teeth, restorations of teeth, restorative material, gingiva, or dental devices, said process comprising the steps of:

coating said dental surface with an intraorally compatible temporary adhesive to form an adhesive dental surface;

mounting said strip onto said adhesive dental surface, such that said strip substantially covers said adhesive dental surface, and such that said strip removably adheres to said adhesive dental surface.

* * * * *